(12) United States Patent
Carleson

(10) Patent No.: US 7,388,218 B2
(45) Date of Patent: Jun. 17, 2008

(54) SUBSURFACE IMAGING USING AN ELECTRON BEAM

(75) Inventor: Peter D. Carleson, Hillsboro, OR (US)

(73) Assignee: FEI Company, Hillsboro, OR (US)

( * ) Notice: Subject to any disclaimer, the term of this patent is extended or adjusted under 35 U.S.C. 154(b) by 327 days.

(21) Appl. No.: 11/098,578

(22) Filed: Apr. 4, 2005

(65) Prior Publication Data

US 2006/0219953 A1   Oct. 5, 2006

(51) Int. Cl.
*H01J 49/00* (2006.01)
(52) U.S. Cl. .................... 250/492.3; 250/492.21
(58) Field of Classification Search ........... None
See application file for complete search history.

(56) References Cited

U.S. PATENT DOCUMENTS

| | | | |
|---|---|---|---|
| 4,785,182 A | 11/1988 | Mancuso et al. | |
| 5,594,245 A | 1/1997 | Todokoro et al. | |
| 6,225,626 B1 | 5/2001 | Talbot et al. | |
| 6,262,430 B1 * | 7/2001 | Li | 250/492.3 |
| 6,281,025 B1 * | 8/2001 | Ring et al. | 438/10 |
| 6,414,307 B1 * | 7/2002 | Gerlach et al. | 250/309 |
| 6,452,176 B1 * | 9/2002 | Davis | 250/310 |
| 6,548,810 B2 | 4/2003 | Zaluzec | |
| 6,709,554 B2 * | 3/2004 | Ferranti et al. | 430/5 |
| 6,768,324 B1 * | 7/2004 | Yamada et al. | 324/751 |
| 6,809,534 B2 * | 10/2004 | Yamada | 324/751 |
| 7,064,822 B2 * | 6/2006 | Borden et al. | 356/239.8 |
| 2002/0074494 A1 | 6/2002 | Lundquist et al. | |
| 2003/0138709 A1 | 7/2003 | Burbank et al. | |
| 2004/0108458 A1 | 6/2004 | Gerlach et al. | |

* cited by examiner

*Primary Examiner*—David A. Vanore
(74) *Attorney, Agent, or Firm*—Scheinberg & Griner, LLP; Michael O. Scheinberg; Robert McMinn

(57) ABSTRACT

A method of navigating or endpointing a microscopic structure by subsurface imaging using a beam of electrons having sufficient energy to penetrate the surface and produce a subsurface image. For endpointing, when the subsurface image become relatively clear at a known electron energy, a user knows that he is approaching the buried feature. For navigating, a subsurface image can be formed of fiducials or other features to determine the position of the beam on the device.

20 Claims, 5 Drawing Sheets

SUBSURFACE IMAGING USING AN ELECTRON BEAM

TECHNICAL FIELD OF THE INVENTION

The present invention relates to methods for navigating, including end pointing, using microscopic features that are buried below the surface of a work piece.

BACKGROUND OF THE INVENTION

Modern integrated circuits are composed of multiple layers of conductors, insulators, and semiconductors. Many modern integrated circuits are fabricated using "flip chip" technology in which the circuit is mounted upside-down onto a carrier. To inspect or alter interior layers of such circuits after the chip is mounted, it is necessary to approach the circuit from the backside. Semiconductor wafers are typically several hundred microns thick, so it is necessary to remove a substantial amount of material from the back side of the circuit before reaching the circuit. When accessing circuitry from the backside, there are no reference points for navigation, that is, there is no easy way to determine exactly where a particular feature on the circuit is located. Thus, to access the circuitry on a flip chip, one must determine where to remove material to expose the circuit from the back side and when to stop removing material to prevent damage to the circuit. Determining when to stop milling is referred to as "end pointing."

Removing the backside material is typically performed in several steps. A first step typically includes a process, such as chemical mechanical polishing, that rapidly thins the entire chip, leaving sufficient material to provide mechanical strength for handling the chip. A subsequent step involves making a large hole in the material centered on the estimated position of the circuit feature of interest. Such a process is typically done using a laser or an ion beam. A process that rapidly removes material is typically not capable of stopping at a precise depth, so as the back side hole approaches the circuit, a second, more accurate process is typically used.

One method of slowing approaching the circuit from the backside uses ion beam milling along with an "end-pointing" technique that indicates when the feature to be exposed is near or is reached. In one end-pointing technique, a light is shown into the hole, and the light induces a current as the hole approaches a transistor region of the circuit. As the optical beam-induced current increases, the user knows that he is getting closer to the transistor region of the circuit.

Another endpointing technique, described in U.S. Published Pat. App. No. 2002/0074494 to Lundquist, uses focused ion beam milling to approach an active transistor region of the circuit from the backside. As the ion beam approaches the circuit, it creates charge carriers that cause a leakage current through the transistor. The ion beam is modulated, and a frequency sensitive amplifier amplifies the power supply leakage current at the modulation frequency. When the current achieves a certain level, the user assumes that the ion beam is very close to the active transistor region of the circuit. While this method can tell when a user is getting close to an active transistor region, it does not provide information about where on the surface the ion beam is impacting, other than that it is impacting near an active transistor region.

One common technique for determining when to stop milling, whether on the back side of a flip chip or on the front side of a conventional circuit, is to observe an image of the circuit when a layer has been milled through. Although an optical microscope can be used to form an image, the resolution of an optical microscope is on the order of 0.5 µm, which is insufficient to observe to circuit features, which can be on the order of 0.1 µm. A more appropriate method of observing microscopic devices is by using charged particle beam imaging, such as scanning ion microscopy or scanning electron microscopy.

A charged particle beam, such as a focused ion beam or an electron beam, is scanned across a surface. The impact of the charged particle beam causes the ejection of various particles, including secondary electrons, backscattered electrons, and ions. The number of particles emitted from each point depends on the composition and the topography at the point. An image is formed on a video monitor, with the brightness of each point on the image corresponding to the number of particles emitted from the surface at a corresponding point. An image can provide information to navigate by, if the image can be correlated to known information about the circuit.

The work piece typically is typically supported on a stage. The stage can move in three dimensions, "X," "Y," and "Z," and movement of the stage and beam is specified and controlled using system coordinates. A work piece typically has its own coordinate system used by its designers to specify where various features are formed. By finding registration marks, known as "fiducials," that are incorporated into the work piece, it is possible to correlate work piece coordinates with system coordinates, so that a user can specify a position on the work piece using work piece coordinate, and the system can move the stage and direct the beam, that is "navigate," to that location. Such correlation is referred to as registration. While milling a chip from the back side, the fiducials are not visible and so it is difficult to register the work piece and to find a desired location.

While imaging techniques are useful for navigating in a plane, such techniques have disadvantages for end pointing. When using imaging to determine when a layer is exposed, the layer can be damaged before the endpoint is determined. Moreover, in order to find reference points in an image to determine where on the circuit the beam is located, it would be necessary to expose by trial and error and relatively large area, potentially damaging each area that is exposed.

U.S. Pat. No. 6,548,810 to Zaluzec for a "Scanning Confocal Electron Microscope" teaches an electron microscope that can image subsurface features, but because the system uses transmitted electrons, the substrate must be relatively thin and the system configured for detecting transmitted electrons, and so cannot be readily used in existing SEMs.

SUMMARY OF THE INVENTION

An object of the invention is to provide a method for subsurface viewing to determine the position of buried microscopic features, for example, to correlate the coordinates of a physical system with the coordinates of an image of the system or with computer design information, or to determine when to stop a milling operation is approaching the buried feature.

When a charged particle beam impacts a surface, secondary electrons and backscattered electrons are generated. The number and quantity of secondary and backscattered electrons provide information about the surface. When an ion beam impacts the surface, the ejected electrons typically provide information about the top few nanometers of the surface (although electrical charging of subsurface can provide some contrast of those features for imaging). When a beam of electrons having relatively high energies is directed toward a surface, the electrons penetrate the surface to a depth that depends on the electron energies, and so the electrons ejected can be indicative of subsurface features.

In a preferred embodiment, an electron beam having sufficiently high energy to penetrate the surface is directed toward a substrate and an image of subsurface features is formed. A user uses the subsurface image to determine the location of the beam impact and to direct the beam to a desired subsurface feature. Unlike focused ion beam imaging, in which the secondary electrons are generated with a few nanometers of the surface, electrons having sufficient energy can penetrate more than a micron into the surface to provide information about subsurface features. The subsurface feature can be, for example, an orientation mark, such as a fiducial on an integrated circuit or any feature. Viewing the fiducial can allow a user to correlate or register between a map of the substrate, such as computer aided design data of an integrated circuit, with the real surface, so that the use can navigate the beam on the surface to a precise location on the real surface using the map.

Because the depth of the viewing is determined by the electron energy, the depth below the surface of the feature viewed can be determined. Thus, the subsurface electron beam viewing can also be used for end pointing, that is, for determining when to cease milling.

Subsurface viewing for alignment is particularly useful for back side navigation in which there is no exposed features to orient on. It is also useful for front side alignment when fiducials or other marks are obscured by a layer.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more through understanding of the present invention, and advantages thereof, reference is now made to the following descriptions taken in conjunction with the accompanying drawings, in which.

DETAILED DESCRIPTION OF PREFERRED EMBODIMENTS

Figure 1:
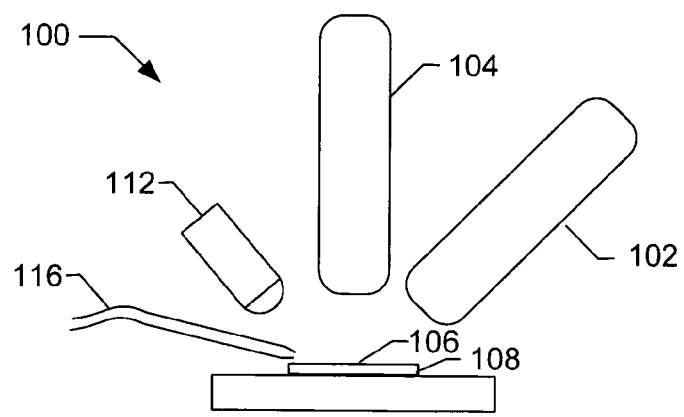
FIG. 1 is shows schematically a dual beam (ion and electron columns) system that can be used to practice a preferred embodiment of the invention.

FIG. 1 shows schematically a dual beam system 100 that is useful for implementing the present invention. One suitable system, for example, is the Model Strata 400 available from FEI Company, the assignee of the present application. The invention can be practiced using any electron beam system having the capability to produce an electron beam having sufficient beam energy, signal detectors, and resolution required for the specific application.

In the embodiment shown, an electron beam column 102 and an ion beam column 104 are oriented at an angle to each other, and the beams produced by each column impinge on the same spot 106 on a substrate 108. In other embodiments, the impact points are separated, and a stage accurately moves the substrate between the beam impact positions. In such embodiments, the beams can be oriented at an angle to each other to reduce the stage travel distance, or the beams could be parallel. In other embodiments, the ion beam and electron beam can be coaxial, as described in U.S. Pat. Publication No. 20040108458. A detector 112 detects secondary electrons emitted from the target as it is impacted by the ion beam or the electron beam. Alternatively, a back scatter electron detector, a through the lens detector, or other detector could be used.

Skilled persons will recognize that system 100 can include many additional features, such as a gas injection system 116 for particle beam deposition or enhanced etching. The substrate 108 is typically maintained in a high vacuum, for example, about $10^{-5}$ Torr ($0.001 N/m^2$) although the invention can be practiced in a low vacuum system, such as an environmental scanning electron microscope, as described in U.S. Pat. No. 4,785,182 to Mancuso et al., which is assigned to the assignee of the present invention. While a preferred embodiment includes a focused ion beam for altering the work piece, the work piece can also be altered by a laser or by an electron beam using appropriate etch-assisting chemicals, so not all embodiments will include a FIB column.

An aspect of the invention includes using an electron beam having sufficiently high energy to form a subsurface image, that is, an image of features that are covered by another material. Electrons energies used in the invention are typically greater than the energies used in scanning electron microscopy, and less than the energies used in transmission electron microscopy. The preferred electron energy will vary with the type of material and the thickness of the covering layer. In various embodiments, electrons having energies greater than about 5 keV, greater than about 10 keV, greater than about 15 keV, greater than about 25 keV, greater than about 30 keV, or greater than about 50 keV may be preferred. The invention is not limited to these specific electron energies; lower energies will be useful for thinner layers and greater energies will be useful for thicker layers.

Figure 2A:
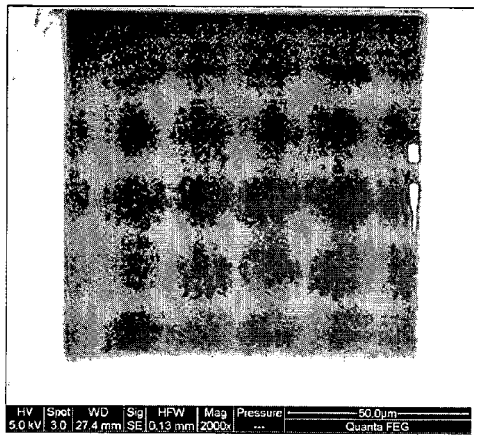
FIGS. 2A-2D shows images formed of a buried metal layers using various electron beam voltages.
Figure 2B:
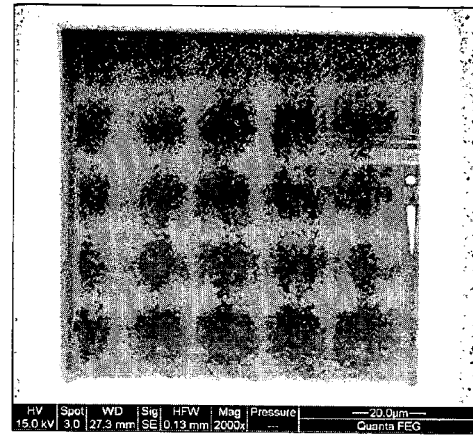
Figure 2C:
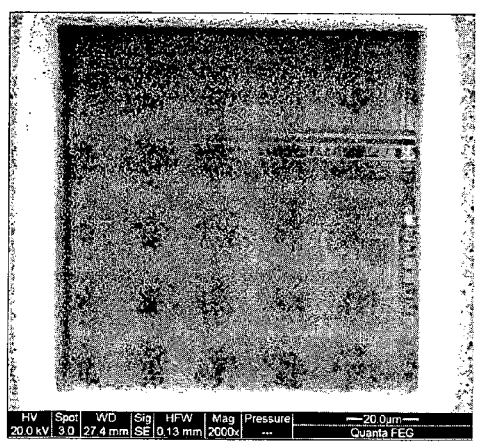
Figure 2D:
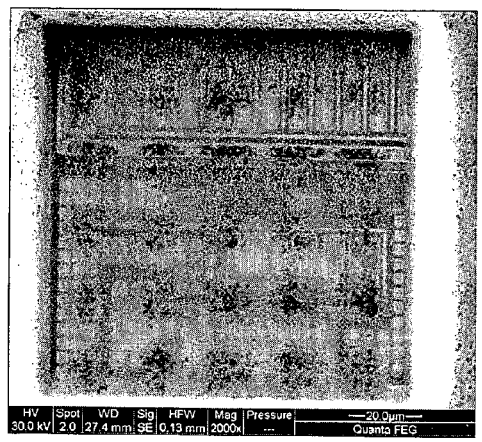
Figure 3A:
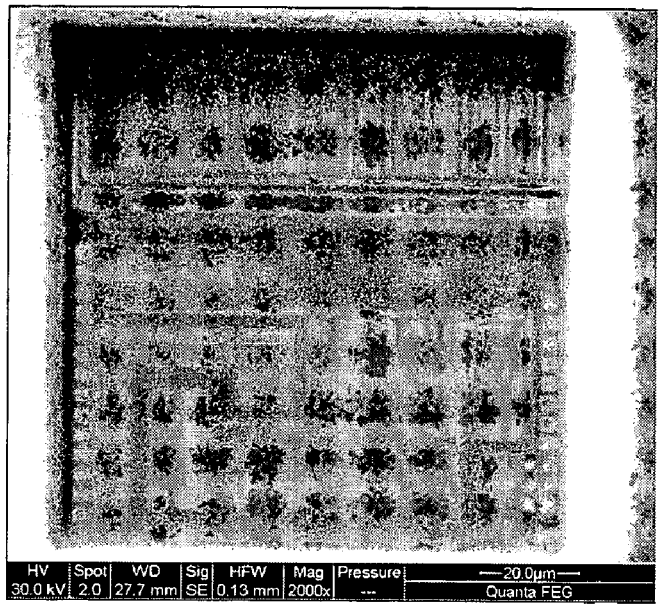
FIGS. 3A and 3B show images of the buried metal layers of FIGS. 2A-2D obtained at different system parameters.
Figure 3B:
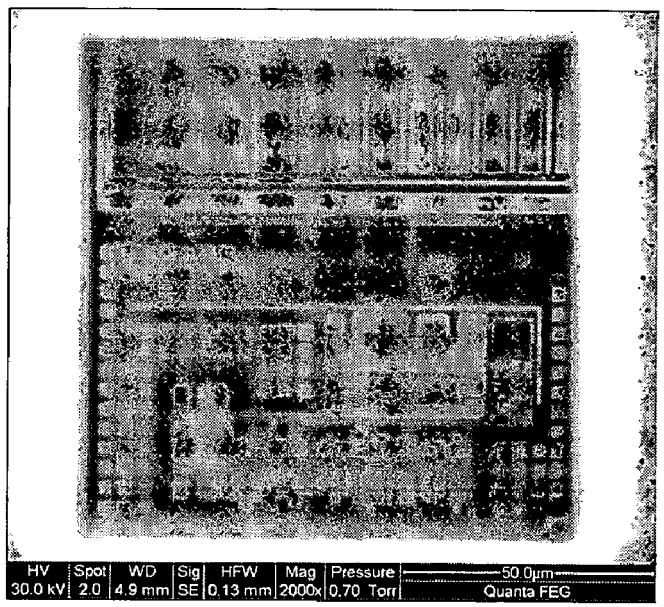

FIGS. 2A-2D show images created using electrons beams of various energies and a secondary electron detector to observe within a trench created by FIB milling using xenon difluoride as an etch-enhancing gas. The substrate shown in FIGS. 2A-2D includes metal lines buried under about 1 μm to 2 μm of silicon with about 1 μm of relatively transparent FIB-deposited silicon oxide over the silicon. FIG. 2A, in which the electron beam forming the image had an acceleration voltage of 5 kV, does not show any detail of the subsurface metal layer. FIG. 2B, in which the electron beam forming the image had an acceleration voltage of 15 kV, begins to show some circuit detail on part of the image, probably because the silicon layer is thinner over that portion of the image, or because of electrical charge build up on parts of the circuit under that portion. FIG. 2C, in which the electron beam forming the image had an acceleration voltage of 20 kV, shows more of the circuit detail is visible. FIG. 2D, in which the electron beam forming the image had an acceleration voltage of 30 kV, shows sufficient circuit detail to navigate about the surface or to correlated the surface with computer aided design data, an optical map of the surface, or other representation The electron beam process parameters can be varied depending on the application to produce a useable image. FIGS. 3A and 3B show images of the same substrate of FIGS. 2A-2D formed by a 30 kV electron beam, varying the pressure in the sample chamber and the working distance, that is, the distance between the electron lens and the work piece. FIG. 3A shows an image taken under a high vacuum, e.g., about $10^{-5}$ Torr (0.0013 N/m$^2$) using a working distance of 27.7 mm, whereas FIG. 3B shows an image taken at a pressure of 0.7 Torr (93 N/m$^2$) and a working distance of 4.9 mm.

Figure 5:
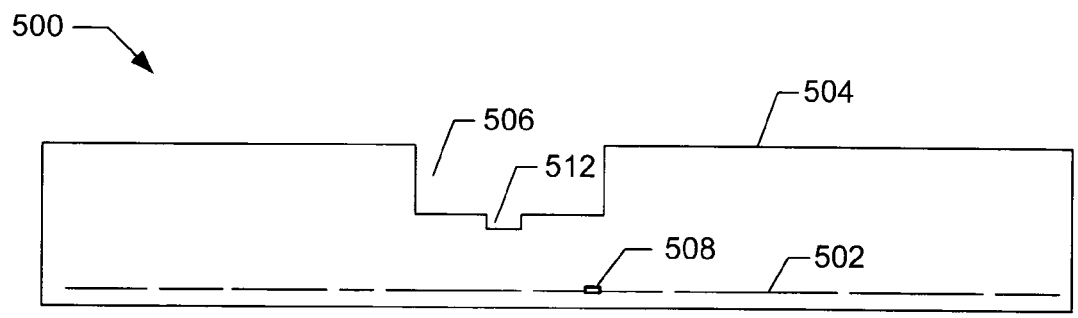
FIG. 5 shows a device being operated upon using the steps of FIG. 4.
Figure 4:
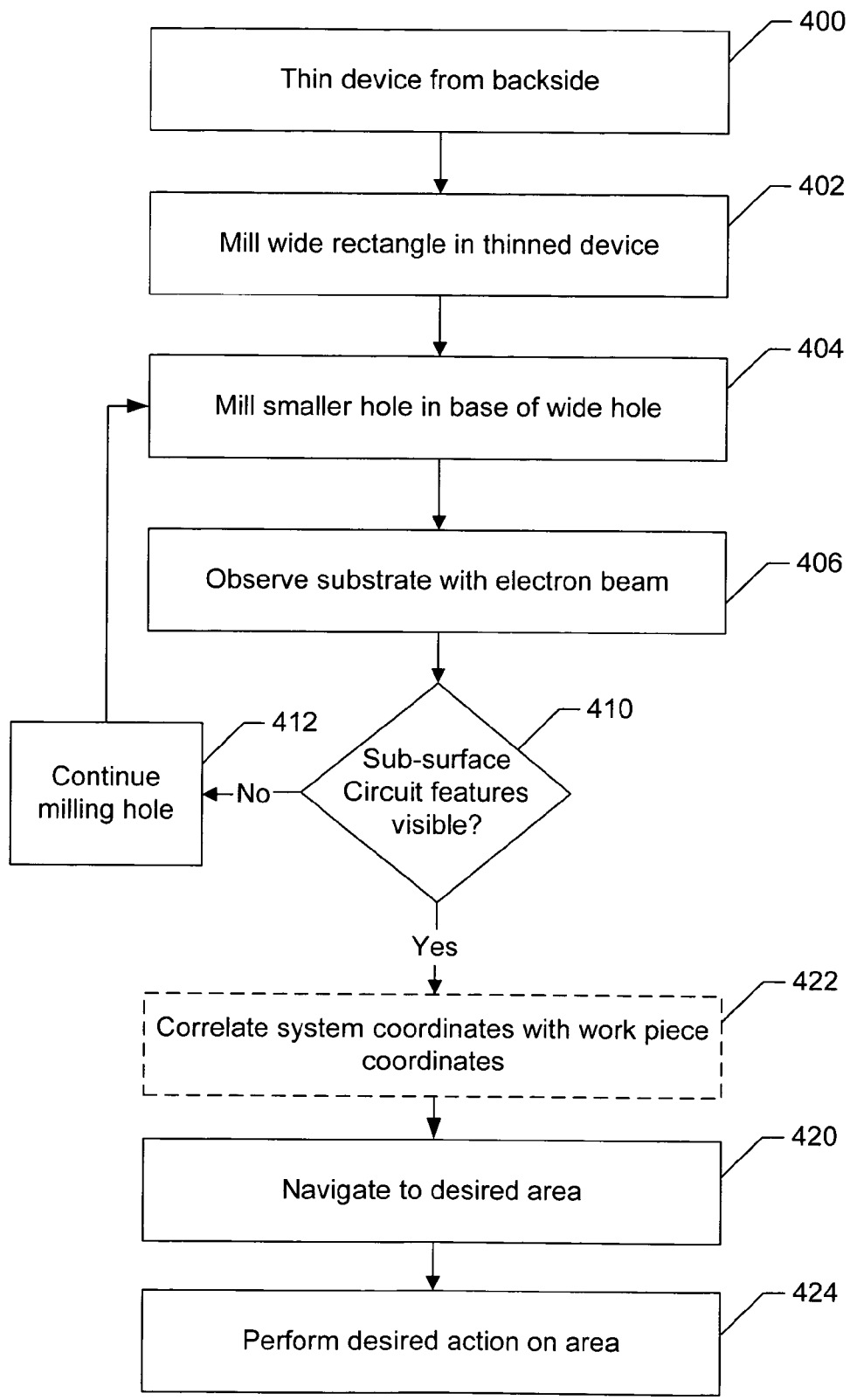
FIG. 4 is a flow chart showing a preferred embodiment for use on a semiconductor device.

According to one aspect of the invention, subsurface imaging can be used to view subsurface features to navigate around the substrate and to determine when to stop milling so as not to damage the substrate. FIG. 4 is a flow chart showing a preferred method of correlating design data to a physical surface on a device to enable navigation around the device. FIG. 5 shows a device 500 on which the steps of FIG. 4 are performed. Device 500 includes buried circuitry including a metal layer 502. In step 400, device 500 is thinned from the back side by 504 chemical mechanical polishing to a thickness of about 200 microns. In step 402, a 200 µm by 200 µm hole 506 about 10-500 µm deep is milled in the device, the hole centered at a point estimated to contain circuitry 504 of interest. In step 404, a 1 µm by 1 µm hole 512 is milled at the bottom of the 506. Periodically, milling is paused and the bottom of the hole 512 is examined in step 406 using an energy electron beam having sufficient energy in an attempt to view subsurface features. The electrons in the beam have energies preferably greater than 15 keV, more preferably greater than 20 keV, even more preferably greater than 25 keV, and most preferably approximately 30 keV or greater, or approximately 50 keV or greater. The electron energy used will depend upon how far below the surface the user wants to view and the capabilities of the electron column.

When the thickness of the covering material is sufficiently thin for subsurface imaging, the electron beam image shows a marked contrast between metal layers, insulating, and semiconducting layers. The contrast between different types of semiconductors is not as great. The invention thus facilitates viewing subsurface metals, which are useful for orienting on the substrate.

As the bottom of hole 512 approaches metal layer 502, as estimated from the milling rate and the thickness of material above the metal layer, the user ceases milling and obtains a subsurface image in step 406 using an electron beam of sufficient energy as described above. At first, if the user is cautious and stops milling well before approaching the metal layer, the electron beam image will typically not show the metal layer as the semiconductor material above the metal layer is too thick to be penetrated by the electron beam. As shown in decision block 410, the user continues milling in step 412 if the metal layer 502 is not visible. As more material is removed, the user periodically obtains subsurface images, repeating steps 404 to 412. As the bottom of hole 512 approaches metal layer 502, the user will at first begin to see in the subsurface image, a faint view of the metal lines.

As the bottom of hole 512 gets closer, the image of the metal layer 502 becomes much clearer, and, depending upon the electron beam energy, the image of metal lines buried under 1 µm to 2 µm of material can be sufficiently clear for a user to determine where on the overall circuit the beam is directed. The user can navigate the beam visually to feature 508 in step 420. Optionally, the user can correlate in step 422 the image of the physical circuit to a known map of the circuit to assist in navigating to a desired feature 508 position on the circuit in step 420. The use can then operate in step 424 on the precise location desired, without damaging other areas in an effort to find the beam location. The degree of clarity of the subsurface image also provides information about the depth of the metal layer below the surface, so the user can ensure that millings ceases before the circuit is unintentionally damaged. Thus, the invention us useful for both navigating in a plane and navigating in three dimensions for endpointing.

In another aspect of the invention, the user uses the subsurface imaging to view buried reference marks to align the physical specimen with a reference image, such as computer aided design data or an optical image taken of a device in a stage of processing when features were exposed. In some processes performed during the fabrication of integrated circuits, a layer is deposited that covers over the fiducials used to align and navigate on the device. While the fiducials are sometimes visible as raised areas in the covering layer, even those signs can be obscured if the surface is "planarized," that is polished to produce a smooth surface to prepare for the next processing layer.

Figure 7:
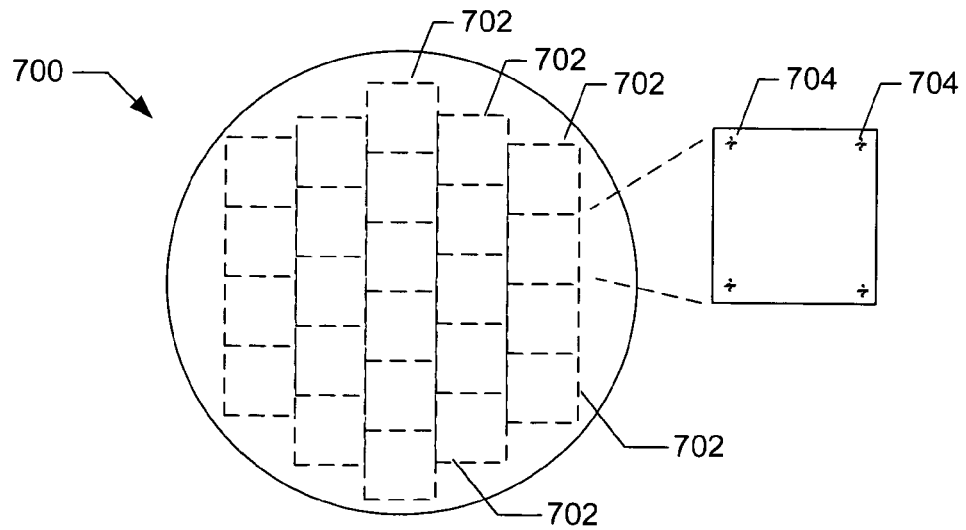
FIG. 7 shows a wafer operated upon by the method shown in FIG. 6.
Figure 6:
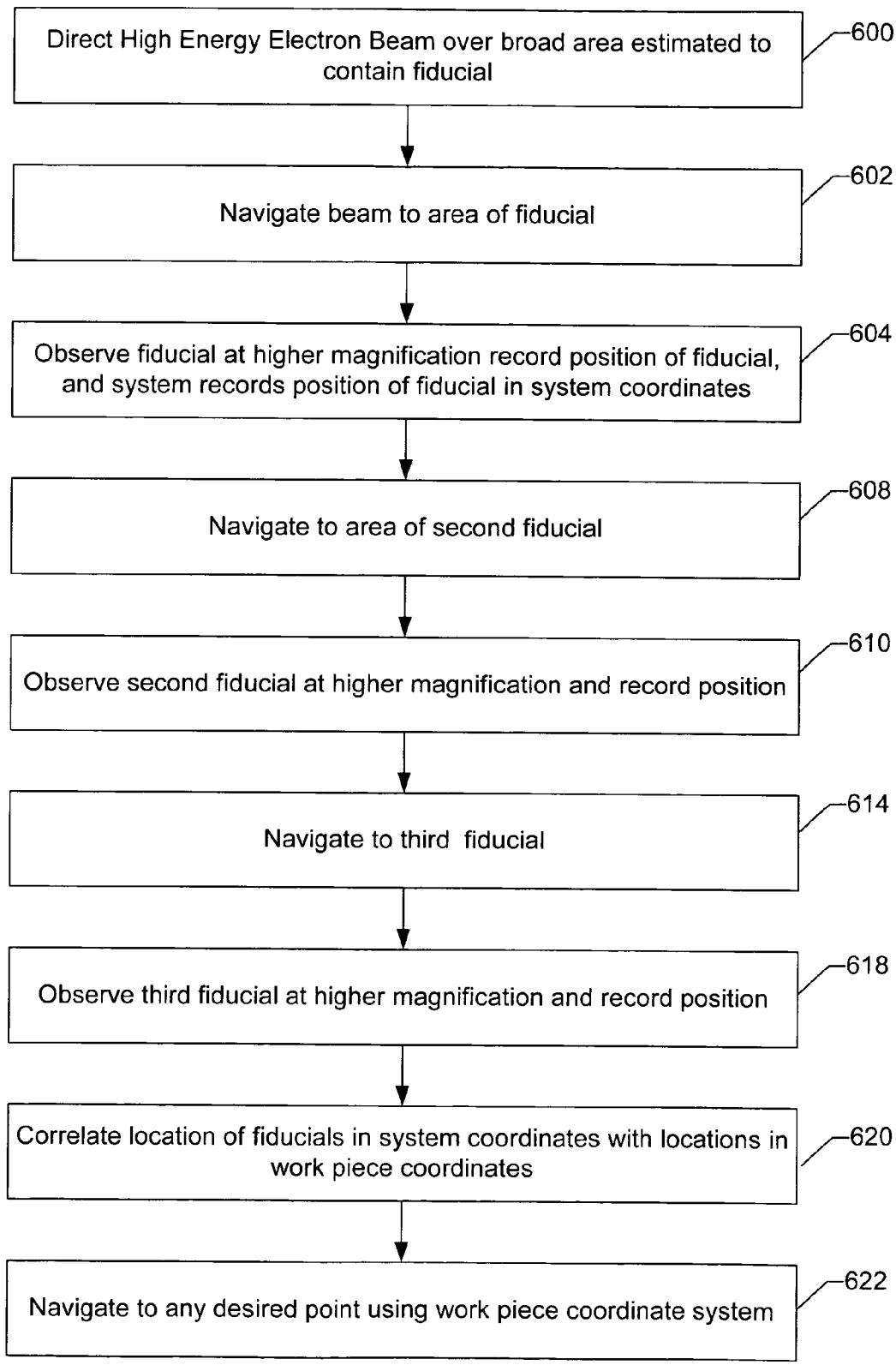
FIG. 6 is a flow chart showing a preferred embodiment for correlating system coordinates with work piece coordinates.

FIG. 6 is a flow chart showing the preferred steps of another embodiment of the invention. FIG. 7 shows a wafer 700 that includes multiple devices or circuits 702, each circuit including multiple fiducials 704 that created on the wafer by the photolithography patterns applied to the wafer to produce the circuit. The circuitry and the fiducials have been covered by a material, such as a metal or insulator, that was deposited onto wafer during a previous fabrication step. In step 600, a user navigates to the area that he has estimated includes a first fiducial 704, and directs a relatively high energy electron beam at low magnification over a broad area to find the fiducial. The electron beam energy is "relatively high," that is, it is typically greater than the energy of an electron beam that is used to image surface features only. In step 602, the user navigates to the area of the fiducial found in step 600. In step 604, the user observes the fiducial at a higher magnification to more precisely determine its position, and the system notes the position of the fiducial on the system coordinates. Based on the position and orientation of the first fiducial, the user can navigate in step 608 to the general area of a second fiducial, and locate the buried fiducial using a relatively high energy electron beam at low magnification. In step 610, observes the second fiducial at increased magnification and the system records its coordinates in the system coordinate system. Typically, the user navigates to a buried third fiducial in step 614, and views the area around the fiducial using a relatively high energy electron beam at low magnification to locate the fiducial. The third fiducial is viewed at increased magnification, and the system notes its coordinates in step 618. In step 620, the location of the fiducials in the system coordinate system are correlated to a work piece coordinate system, such as data from a computer aided design (CAD) database or inspection system, such as another microscope with accurate stage positioning and position readouts that can be used to determine coordinates. In step 622, the user navigates to any point on the work piece, using the CAD coordinates of the point, which are translated into system coordinates to move the work piece stage and direct the beam.

The process described in the flow chart in FIG. 6 can readily be automated using image recognition software, such as that available from Cognex Corporation, Natick, Mass.

The term "navigate" is used herein to include not only determining a position and moving in the X and Y direction on a substrate, but also include determining a vertical position to assist endpointing, that is, to determining when to stop milling as one approaches a buried feature. The invention is not limited to use on integrated circuits, but is useful for any multilayer, substrate that includes microscopic features covered by another material.

Although the present invention and its advantages have been described in detail, it should be understood that various changes, substitutions and alterations can be made herein without departing from the spirit and scope of the invention as defined by the appended claims. For example, the invention is not limited to the integrated circuit examples described above, but is useful for any type of microscopic device having buried features. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. A method of processing a semiconductor device using ion beam milling and electron beam imaging, comprising:
   directing a focused ion beam toward a semiconductor device to mill a hole approaching a buried metal layer;
   directing toward the bottom of the hole an electron beam having sufficiently energetic electrons to obtain a subsurface image and collecting electrons ejected away from the hole to view the subsurface image of the metal layer through at least 0.1 µm of silicon; and
   using the image of the metal layer to determine when to stop milling with the focused ion beam.

2. The method of claim 1 further comprising using the subsurface image to identify a subsurface feature for orienting or for processing.

3. The method of claim 2 in which using the subsurface image to locate a feature for orienting or for processing includes correlating the image to a map of the device.

4. The method of claim 1 in which the electrons in the electron beam have an average energy greater than 15 kV.

5. The method of claim 4 in which the electrons in the electron beam have average energies greater than 25 kV.

6. A method of navigating a work piece, comprising:
   scanning on the work piece an electron beam having sufficiently high energy to produce an image of one or more subsurface features from secondary or backscattered electrons; and
   using the subsurface image to navigate on the work piece.

7. The method of claim 6 in which using the subsurface image to navigate on the work piece includes correlating the one or more subsurface features to known information about the work piece.

8. The method of claim 7 in which correlating the one or more subsurface features to known information about the work piece includes correlating the one or more subsurface features to computer design information for the work piece.

9. The method of claim 6 in which the electrons in the electrons beam have an average energy greater than 15 kV.

10. The method of claim 6 in which the electrons in the electron beam have an average energy greater than 25 kV.

11. The method of claim 6 in which the depth of material covering the subsurface feature is greater than 0.5 µm.

12. The method of claim 11 in which the depth of material covering the subsurface feature is between 0.5 µm and 2.0 µm.

13. In a process of using a focused beam to cut a hole in a substrate to expose for imaging or alteration a subsurface, microscopic feature, the improvement comprising determining the location of the subsurface feature or determining when a beam is about the to expose the subsurface feature by forming a subsurface image of the feature by directing toward the surface covering the subsurface feature an electron beam having a sufficiently high energy to produce an image of the subsurface, microscopic feature from secondary or backscattered elections.

14. The process of claim 13 in which the electrons in the electron beam have an average energy greater than 15 kV.

15. The process of claim 14 in which the electrons in the electron beam have an average energy greater than 25 kV.

16. The process of claim 15 in which the electrons in the electron beam have an average energy greater than 30 kV.

17. The process of claim 13 in which the microscopic subsurface feature comprises a metal.

18. The process of claim 13 in which the depth of material covering the subsurface feature is greater than 0.5 µm.

19. The process of claim 13 in which the depth of material covering the subsurface feature is between 0.5 µm and 2.0 µm.

20. The process of claim 13 further comprising ceasing using the focused beam to cut the hole when the beam is about to expose the subsurface feature.

* * * * *